(12) United States Patent
Bachert

(10) Patent No.: US 11,020,043 B2
(45) Date of Patent: Jun. 1, 2021

(54) DEVICE FOR PERFORMING AN ALLERGY TEST

(71) Applicant: PROF. DR. CLAUS BACHERT BVBA, St Martens-Latem (BE)

(72) Inventor: Claus Bachert, St. Martens-Latem (BE)

(73) Assignee: PROF. DR. CLAUS BACHERT BVBA, St Martens-Latem (BE)

( * ) Notice: Subject to any disclaimer, the term of this patent is extended or adjusted under 35 U.S.C. 154(b) by 564 days.

(21) Appl. No.: 15/753,155

(22) PCT Filed: Aug. 21, 2015

(86) PCT No.: PCT/EP2015/069283
§ 371 (c)(1),
(2) Date: Feb. 15, 2018

(87) PCT Pub. No.: WO2017/032400
PCT Pub. Date: Mar. 2, 2017

(65) Prior Publication Data
US 2018/0249942 A1 Sep. 6, 2018

(51) Int. Cl.
*A61B 5/00* (2006.01)
*A61B 10/00* (2006.01)
(Continued)

(52) U.S. Cl.
CPC ............ *A61B 5/411* (2013.01); *A61B 5/6849* (2013.01); *A61B 5/6886* (2013.01);
(Continued)

(58) Field of Classification Search
CPC ... A61B 5/411; A61B 10/0035; A61B 17/205; A61B 17/32093; A61B 17/10; A61M 5/46
See application file for complete search history.

(56) References Cited

U.S. PATENT DOCUMENTS 3,289,670 A * 12/1966 Krug .................... A61B 17/205
600/556
4,270,548 A * 6/1981 Brennan .............. A61B 17/205
206/439
(Continued)

FOREIGN PATENT DOCUMENTS

CA 2169661 A1 3/1995
JP H04501212 A 3/1992
(Continued)

OTHER PUBLICATIONS

Allergy Diagnostic Testing, WAO World Allergy Testing, Dr. John Oppenheimer et al., Jul. 2014 (Year: 2014).*
(Continued)

*Primary Examiner* — Sean P Dougherty
(74) *Attorney, Agent, or Firm* — Christensen O'Connor Johnson Kindness PLLC

(57) ABSTRACT

A device (10) for performing an allergy test comprising a container unit (11) having a first surface (12) and a second surface (13). The container unit (11) comprising a plurality of cavities (22) each arranged for receiving an allergen container (14) comprising a supporting material (18) and a pricking tool, which is secured at a location of the supporting material (18). The supporting material (18) is arranged, when a pressure force is applied on the second surface (13), for being compressed thereby causing the pricking tool (19) for being displaced from a first position (25), wherein at said first position the at least one pricking tip (24) is at a first distance from the first surface (12), to a second position (26), wherein at said second position (26) the at least one pricking tip (24) is at a second distance from the first surface (12).

23 Claims, 11 Drawing Sheets

(51) Int. Cl.
*A61B 17/20* (2006.01)
*A61M 5/46* (2006.01)
*A61B 17/3209* (2006.01)
*A61M 35/00* (2006.01)
*A61M 37/00* (2006.01)

(52) U.S. Cl.
CPC ........ *A61B 10/0035* (2013.01); *A61B 17/205* (2013.01); *A61B 17/32093* (2013.01); *A61M 5/46* (2013.01); *A61B 17/20* (2013.01); *A61M 35/00* (2013.01); *A61M 37/00* (2013.01)

(56) References Cited

U.S. PATENT DOCUMENTS

| | | | | |
|---|---|---|---|---|
| 4,304,241 | A * | 12/1981 | Brennan | A61B 10/00 600/556 |
| 4,711,247 | A * | 12/1987 | Fishman | A61B 17/205 600/556 |
| 5,027,826 | A * | 7/1991 | Fishman | A61B 17/205 600/556 |
| 5,097,810 | A * | 3/1992 | Fishman | A61B 5/411 600/556 |
| 5,099,857 | A | 3/1992 | Baldo et al. | |
| 5,139,029 | A * | 8/1992 | Fishman | A61B 5/411 600/556 |
| 5,154,181 | A * | 10/1992 | Fishman | A61B 17/205 600/556 |
| 5,335,670 | A * | 8/1994 | Fishman | A61B 17/205 600/556 |
| 5,588,441 | A | 12/1996 | Fishman | |
| 7,631,765 | B2 * | 12/2009 | Hein | A61B 5/411 206/470 |
| 9,011,350 | B2 * | 4/2015 | Hein, Jr. | A61B 5/445 600/556 |
| 9,033,898 | B2 * | 5/2015 | Chickering, III | A61B 5/150389 600/573 |
| 2006/0047242 | A1 * | 3/2006 | Laurent | A61B 17/205 604/46 |
| 2006/0167375 | A1 * | 7/2006 | Terrassse | A61B 5/441 600/556 |
| 2007/0118077 | A1 * | 5/2007 | Clarke | A61M 5/158 604/117 |
| 2008/0214952 | A1 * | 9/2008 | Mir | A61M 37/0015 600/556 |
| 2009/0118638 | A1 * | 5/2009 | Schindlbeck | A61B 17/205 600/556 |
| 2010/0022910 | A1 | 1/2010 | Lane et al. | |
| 2010/0100005 | A1 * | 4/2010 | Mir | A61B 5/685 600/556 |
| 2010/0121307 | A1 * | 5/2010 | Lockard | A61M 37/0015 604/506 |
| 2012/0089048 | A1 * | 4/2012 | Harish | A61B 5/411 600/556 |
| 2012/0101406 | A1 * | 4/2012 | Win | A61B 5/411 600/556 |
| 2014/0268318 | A1 * | 9/2014 | Mandella | G02B 21/0048 359/364 |
| 2014/0276196 | A1 | 9/2014 | Niederauer et al. | |
| 2015/0126898 | A1 * | 5/2015 | Sullivan | A61B 5/411 600/556 |
| 2015/0289794 | A1 * | 10/2015 | Smollar | A61B 50/33 600/556 |
| 2015/0342514 | A1 * | 12/2015 | Easton | A61B 5/411 600/556 |
| 2016/0030114 | A1 * | 2/2016 | Patterson | A61B 5/411 600/556 |

FOREIGN PATENT DOCUMENTS

| | | |
|---|---|---|
| JP | H09505210 A | 5/1997 |
| JP | 2007014594 A | 1/2007 |
| JP | 2014023697 A | 2/2014 |
| WO | 88/09149 A1 | 12/1988 |
| WO | 95/05776 A1 | 3/1995 |
| WO | 99/34739 A1 | 7/1999 |
| WO | 2014/036539 A1 | 3/2014 |
| WO | 2016/061600 A1 | 4/2016 |

OTHER PUBLICATIONS

International Preliminary Report on Patentability dated Nov. 20, 2017, issued in corresponding International Application No. PCT/EP2015/069283, filed Aug. 21, 2015, 7 pages.

International Search Report dated Jun. 1, 2016, issued in corresponding International Application No. PCT/EP2015/069283, filed Aug. 21, 2015, 3 pages.

* cited by examiner

DEVICE FOR PERFORMING AN ALLERGY TEST

TECHNICAL FIELD

The present invention relates to a device for performing an allergy test on the patient's skin, and more specifically to a device provided with a pricking tool arranged for penetrating the patient's skin to a predetermined depth so as to optimise, based on the predetermined allergen concentration, the delivery of the allergen, in particular of the officially registered allergens, to the patient's skin.

BACKGROUND ART

Devices for performing an allergy test on the patient's skin are known for example from CN102908123, whereby a device for performing an allergy test is disclosed that can be attached to the patient's skin. The device comprises a container unit provided with a plurality of allergen containers, each containing a predetermined allergen to be delivered to the patient's skin. Each allergen container is provided with a needle fixed at the bottom of the allergen container and completely embedded in a spongy-like material, which contains the allergen. The container is further provided with a structure forming the sidewall of the container. The container unit is provided on a first surface with flexible paste layer, which is arranged for forming a substantially flat skin contact surface arranged for coming into contact with the patient's skin. The flexible paste layer may be arranged for releasably connecting the container unit with a protective foil, which is arranged for sealing the container unit prior to application of the device on the patient's skin. In order to perform the allergy test with the device of the prior art, the protective foil is removed from the flexible paste layer, and the device is applied on the patient's skin. A pressure force is then applied on the bottom side of the container unit, thereby causing the bottom wall of the allergen container to deform. Due to the bottom wall deformation, the needle fixed at the bottom of the allergen container is displaced from a first position, wherein at said first position the needle tip is embedded in the spongy-like material, to a second position, wherein in said second position the needle tip is arranged for protruding from the skin contact surface. At the second position the needle is arranged for penetrating the patient's skin to a predetermined depth so that the allergen contained in the spongy-like material can be delivered to the patient's skin. In general, when performing an allergy test and in order to optimise the skin's response to the allergen delivered, the skin must be penetrated by the needle at a predetermined depth. The predetermined depth is to a large extent determined by the concentration of the allergen to be delivered, in particular by the required concentration of officially registered allergens. In the device of the prior art, the penetration depth of the needle is shown to be identical for all allergen containers irrespective of their allergen concentration. Therefore the penetration depth of the needle is not optimised to the concentration of the allergen contained in the allergen container. As a result, with the device of the prior art the penetration depth achieved at the location of each individual allergen container cannot be matched to the allergen concentration contained in the respective allergen container. This is because the only way to optimise the penetration depth of the device of the prior art is by adjusting the height of the ring shaped wall structure and/or the depth of the bottom wall of the allergen container. Therefore, in the case where the device of the prior art is provided with allergen containers containing allergens at different concentrations, the only way to optimise the penetration depth of the needle at the location of each container would be by adapting the height of the ring shaped wall structure and/or the depth of the bottom wall of the container. However, such an adjustment may lead to either a highly uneven skin contact surface, due to the different heights of the sidewall structures of each allergen container on the container unit, and/or a complex manufacturing process for providing each allergen container with a bottom wall having a different degree of deformation, which will lead to a higher manufacturing cost. The uneven skin contact surface is highly undesirable because it will lead to poor contact of the device to the patient skin, which will affect the penetration depth of the needle. Further, an uneven skin contact surface would further lead to poor contact between the container unit and the protective foil, thereby affecting the sealing of the container unit leading to poor long term stability of the allergens. Therefore, the device of the prior art can at best be optimised for allergens having an identical concentration. However, such an optimisation would further lead to a more complex and expensive manufacturing process, since for each allergen concentration the device parameters, such as the height of the side wall structure and/or the depth of the bottom wall, would need to be adapted accordingly.

DISCLOSURE OF THE INVENTION

It is an aim of the present invention to provide a device for an allergy test wherein the penetration depth at the location of each allergen container can be optimised to the predetermined concentration and amount of the allergen, in particular to the required concentration of an officially registered allergen, contained in the allergen container.

For the purpose of the present invention, the term "allergen" refers to any compound, chemical substance, or biological material, such as proteins, which is capable of evoking an allergic reaction. Allergens are usually understood as a subcategory of antigens, which are compounds, substances, or materials capable of evoking any immune response. In particular, the allergen may be selected, inter alia, from natural or native allergens, modified natural allergens, synthetic allergens, recombinant allergens, modified allergens, allergoids, and mixtures or combinations thereof.

It is further understood that the term "officially registered allergen" refers to allergens which are registered, mostly as a drug, for the diagnosis of allergies by the health authorities. Registered allergens for diagnostic purposes are allergens of high quality, conformity and stability, which have demonstrated suitability for allergy testing, are object to regulatory procedures, and have obtained market registration by the national and/or international health authorities. The documentation submitted for registration of allergen preparations as pharmaceutical specialties must satisfy the general directives formulated by the drug control authorities.

This aim is achieved according to the invention with the device for performing an allergy test showing the technical characteristics of the first claim.

More specifically, according to embodiments of the present invention a device for performing an allergy test for type I immune reactions, such as inhalant allergies, is provided. The device is provided with a container unit provided with a first surface arranged for coming in contact with the skin of a patient undergoing the test and a second surface provided opposite to the first surface. The container unit is provided with a plurality of cavities, each arranged for receiving an allergen container provided with a predetermined allergen in a predetermined concentration. For example and without any limitation, the container unit may be provided with a number of allergen containers carrying allergens at varying concentrations. It should be understood that the allergen containers may be further arranged to carry other type of pharmaceutical solution that need to be delivered to the patient's skin, such histamine, NaCl, and the like. The allergen container is provided with a supporting material and a pricking tool of a predetermined length having at least one pricking tip facing in the direction of the cavity opening. The pricking tool is arranged to be secured at a location of the supporting material e.g. the base of the pricking tool may be fixed at the bottom surface of the supporting material or at another preferred location therein. The supporting material is arranged, when a pressure force is applied on the second surface of the device, for being compressed thereby causing the pricking tool for being displaced from a first position, wherein at said first position the at least one pricking tip is at a first distance from the first surface e.g. embedded in the supporting material, to a second position, wherein at said second position the at least one pricking tip is at a second distance from the first surface. During displacement of the pricking tool, the allergen is arranged for being released from a storage location in the allergen container, e.g. from the supporting material, thereby allowing the allergen to cover the tip of the pricking toll so that the allergen can be delivered in the patient's skin. According to embodiments of the present invention, the supporting material is arranged for controlling the range of displacement of the pricking tool between the first and second positions.

It has been found that by securing the pricking tool at a location of the supporting material, the range of displacement of the pricking tool between the first and second positions may be controlled by the properties of the supporting material. For example, the base of the pricking tool, which is at an opposite end to the pricking tip, may be secure or releasably fixed at the bottom surface of the supporting material, wherein the bottom surface of the material may be arranged for coming in contact with the bottom wall of the cavity. As a result, the penetration depth of the pricking tool, which is determined by the distance between the pricking tip and the first surface at the second position, may be optimised for a predetermined allergen concentration by simple replacing the supporting material of the allergen container with another supporting material, the properties of which have been optimised according to the desired penetration depth to be achieved. Therefore, with the device of the present invention, each allergen container in the container unit can be easily optimised for delivering an allergen of a predetermined concentration to the patient's skin, while ensuring that the skin contact surface of the container unit is maintained substantially flat and while maintaining the overall process of manufacturing the device relative simple. Furthermore, with the device of the present invention, the container unit can be made as a generic container unit, which can be used with allergens of different concentrations, thereby reducing the complexity and cost of manufacturing compared to the device of the prior art. This is because, with the device of the present invention, the penetration depth required for each allergen concentration may be simply optimised by replacing the allergen containers to be received in the cavities of the container units, with allergen containers that have been optimised for the allergen concentration required. Therefore, and contrary to the device of the prior art, the container unit of the device may be manufactured in bulk quantities using the same manufacturing process, since the penetration depth optimisation can be achieved by simply providing in the container unit cavities allergen containers that have been adapted for the required allergen concentration.

According to embodiments of the present invention, the allergen container is adapted such that at the second position the pricking tip of the pricking tool extends over the first surface of the container unit by a predetermined distance, which predetermined distance defines the penetration depth of the pricking tool in the patient's skin. For example, the compressibility of the supporting material may be chosen such that at the second position the pricking tip of the pricking tool extends over the first surface of the container unit by a predetermined distance. Moreover, the height of the supporting material may be chosen such that at the second position the pricking tip extends over the first surface of the device by a predetermined distance. Furthermore, the length of the pricking tool may be chosen based on the compressibility and height of the supporting material and concentration of the allergen such that at the second position the pricking tip extends over the first surface of the device by a predetermined distance.

Within the context of the present invention the term compressibility should be understood as the relative volume change of the supporting material in response to a pressure change.

It is has been found that by adapting the allergen container, the penetration depth of the pricking tool can be easily optimised for different allergen concentrations. This may be achieved by adapting the properties of each allergen container, which may include but not limited to the compressibility and/or the height of the supporting material, the length of the pricking tool, and/or the concentration of the allergen. The compressibility of the supporting material can be for example adapted by providing a supporting material having different compressibility characteristics. The container unit may comprise a plurality of allergen containers, each adapted such that the penetration depth of the pricking tool is adapted to the allergen concentration contained in the allergen container so that the skin response of the patient to the allergen is optimised. For example, each allergen container may be provided with a supporting material having the same height but different compressibility properties, or having different heights or any combination thereof. Also the length of the needle and the location where it is secured at the supporting material, e.g. at the bottom surface or at a location within the supporting material, may be adapted. For example, in one allergen container the base of the pricking tool may be secured at the bottom surface of the allergen material, while in another the pricking tool may be secured at an intermediate location of the supporting material.

According to embodiments of the present invention, the pricking tip is arranged at the second position for extending over the first surface by a distance of preferably between 0.5 mm and 1.2 mm, more preferably between 0.7 mm to 1.0 mm, and even more preferably 0.8 mm.

It has been found that at these distance ranges the allergen delivery to the patient's skin is optimised, thereby enhancing the skin response to the allergen. Furthermore, by adjusting the penetration depth of the needle, the skin response to the allergen may also be adjusted. For example, an allergen at a given concentration may cause a different skin response depending on the penetration depth to which it is delivered, e.g. faster reaction or stronger response, etc.

According to embodiments of the present invention, the supporting material may be a material that can be compressed. Furthermore, the supporting material may be arranged for storing the allergen to be delivered to the patient's skin. For example, the supporting material may be a spongy material, which may be made from any suitable material known to the skilled person in the art such as polymer based materials such as foam, sponge-like non-woven cotton fabric material such as fleece, and the like. For example, in order to achieve a predetermine penetration depth the allergen container may be provided with a supporting material having the desired compressibility characteristics.

According to embodiments of the present invention, the pricking tool may be provided with at least one needle having at least one pricking tip, e.g the needle may be provided with a plurality of tips, e.g three tips. It has been found that by providing a prickling tool with more than one tip, the allergen delivery to the patient's skin can be optimised so as to enhance the skin response to the allergen. For example, by providing a pricking tool with a plurality of tips, the patient's skin is penetrated at multiple closely spaced locations, thereby allowing the allergen to be delivered more effectively and in higher amounts to the skin, thereby optimising the skin response. For example, by providing a pricking tool with four tips, the amount of allergen delivered to the skin would be four times higher compared to the same allergen being delivered by a pricking tool having only one tip. Moreover, a pricking tool with a plurality of tips may increase the skin response to allergens provided at low concentrations because it allows a higher quantity of the allergen to be delivered to the skin.

According to embodiments of the present invention, the pricking tool may be provided with a hollow body forming a canal opening. In this way, the allergen may be delivered directly and in higher amounts into the skin of the patient, thereby optimising the response of the patient's skin to the allergen. For example, by delivering the allergen directly into the skin may result in a faster and stronger response of the skin to the allergen, thereby minimising the time required for performing the allergy test.

According to embodiments of the present invention, the allergen container is provided with a frame. The frame may be arranged for supporting and/or securing the supporting material and for limiting, when pressed on the patient's skin, the wheel response of the skin to the allergen delivered. In this way, the wheel response is maintained within a confined area, thereby ensuring that the skin reaction is limited to a size which is easily identifiable, but not bothering the patient by strong itchy reactions, and additionally limiting the risk of large skin responses confluencing with other allergen areas. This may also limit the risk of systemic adverse events in the patient, as the allergen is hold at a confined area. The frame may be arranged for surrounding the supporting material so as to form the sidewall of the allergen container.

According to embodiments of the present invention, the first surface of the container unit may comprise a flexible adhesive layer arranged for releasably securing the device to the patient's skin. Furthermore, a protective foil may be releasably secured on the first surface by the flexible adhesive layer. The protective foil may be arranged for hermetically sealing the container unit, thereby ensuring the long term stability of the allergens.

According to embodiments of the present invention, the protective foil is made from a non-absorbent material such as polyethylene, polypropylene, aluminium, and the like. In this way, it is ensured that the stability and concentration of the allergen are maintained within acceptable levels during storage of the device, since any absorption of the allergen by the protective foil is prevented. Furthermore, in order to ensure the stability and concentration of the allergen, the support material and/or the protective foil may be provided with a coating layer. For example, the coating layer may comprise allergen or human serum albumin up to 2%. The coating layer may comprise any of streptavidin-biotin, streptavidin-horseradish peroxidase, sugars, two component polymer mix or silicone. The allergen may comprise glycerol up to 50% or Triton-X 100 to keep the allergen in solution and avoid adsorption to the supporting material or foil.

BRIEF DESCRIPTION OF THE DRAWINGS

The invention will be further elucidated by means of the following description and the appended figures.

MODES FOR CARRYING OUT THE INVENTION

Figure 1:
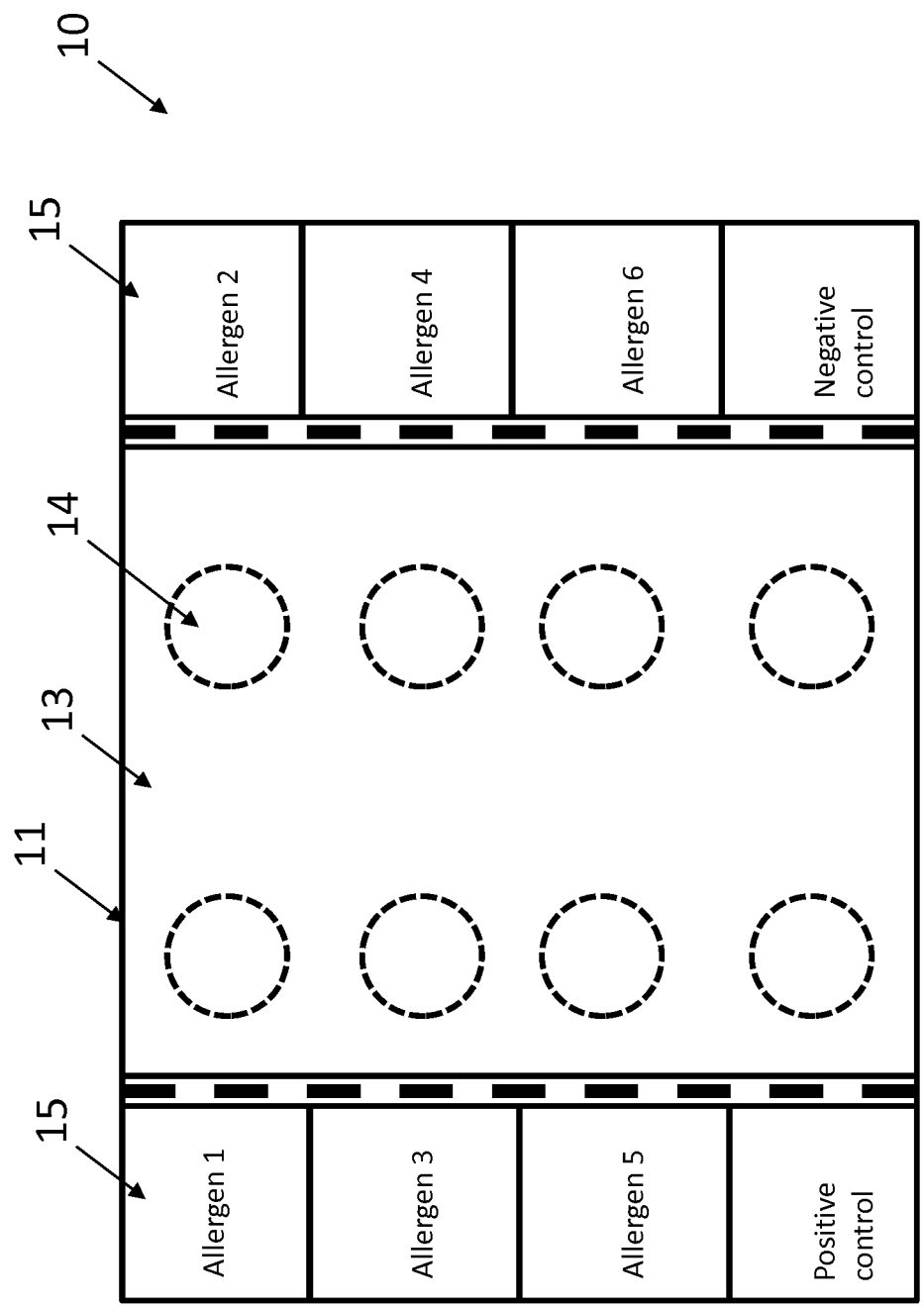
FIG. 1 shows schematically a top view of the second surface of the device for performing an allergy test according to embodiments of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The present invention will be elucidated by means of the example embodiments shown in FIGS. 1 to 10, which will be described in more details below.

Figure 2:
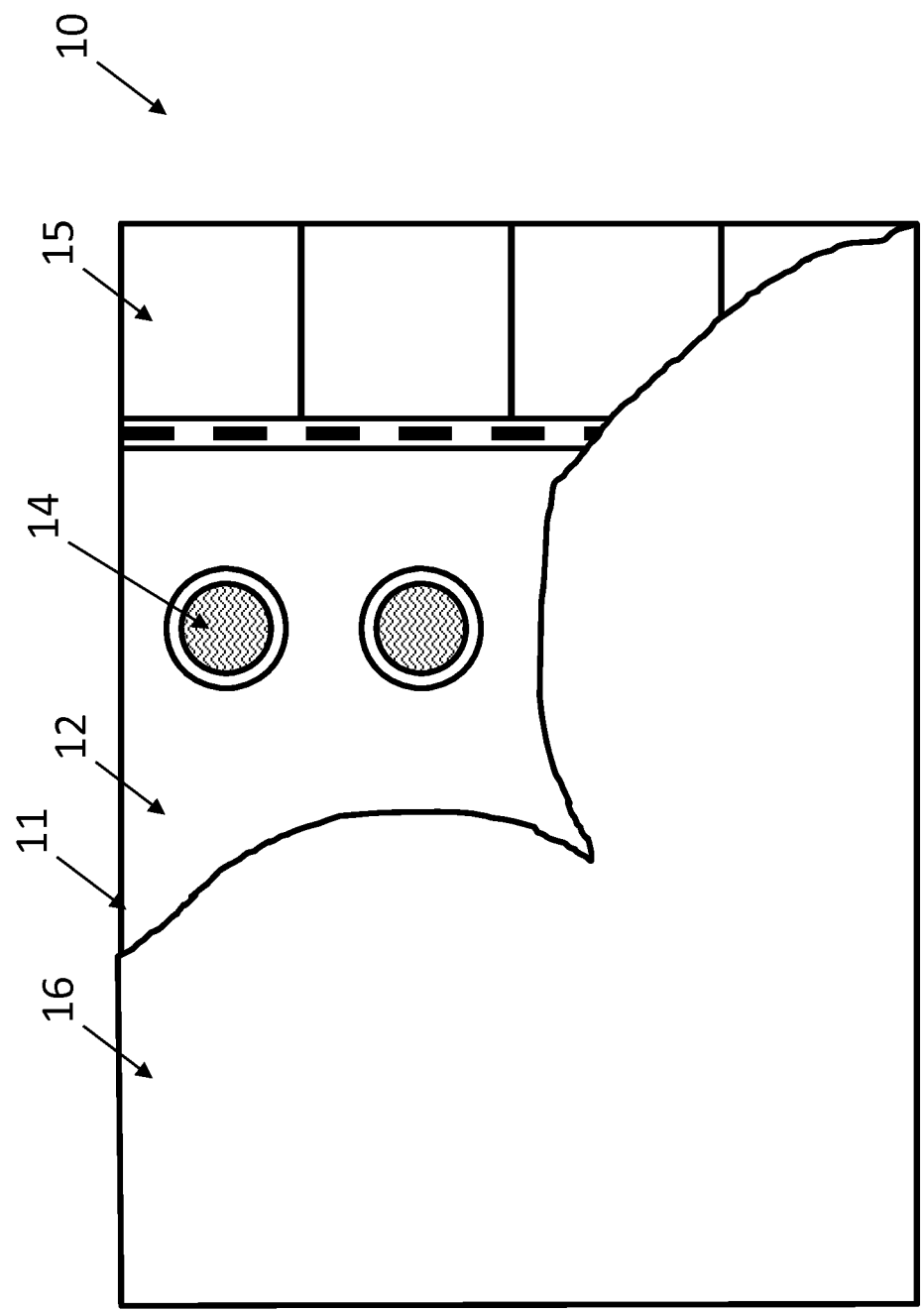
FIG. 2 shows schematically a top view of the first surface of the device for performing an allergy test according to the embodiments of the present invention.
Figure 3:
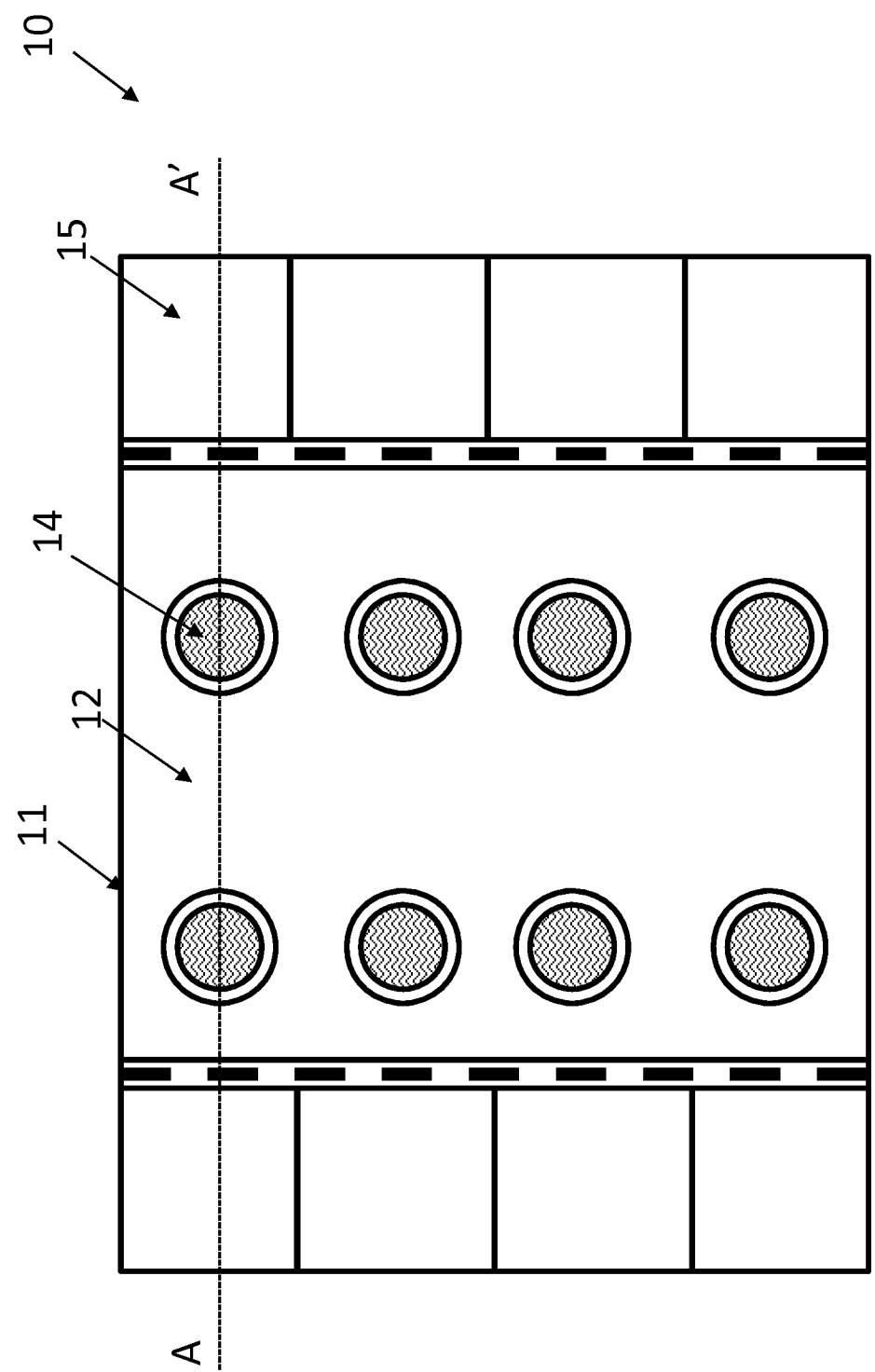
FIG. 3 shows schematically a top view of the first side of the device for performing an allergy test with the protective film removed from the first surface according to embodiments of the present invention.

FIGS. 1 and 2 show top views of respective first and second surfaces of a device (10) for performing an allergen test for type I immune reactions such as inhalant or food allergies according to embodiments of the present invention. As shown in FIGS. 1 and 2, the device 10 may be provided with a container unit 11 having a substantially flat first surface 12, e.g. a skin contact surface, arranged for coming into contact with the skin of a patient 23 undergoing the test. A second surface 13 may be provided opposite the first surface 12. The container unit 11 may be provided with a plurality of cavities 22 e.g. at least four, each arranged for receiving an allergen container 14. For example the container unit 11 may be provided with eight cavities 22, as shown in FIGS. 1 and 2. Each allergen container 14 may be provided with an allergen having a predetermined concentration. For example, the allergen may be an allergen having a registered concentration, which may be arranged, when delivered to the patient's skin 23, for causing a predetermined reaction. The container unit 11 may also be provided with allergen containers containing pharmaceutical solutions arranged for performing a positive and a negative control test, as shown in FIG. 1. For example, some of the allergen container 14 in the container unit 11 may be arranged to perform a positive control test e.g. by delivering to the patient skin a histamine solution, and/or a negative control test e.g. by delivering to the patient's skin a NaCl solution. In order to be able to easily identify the locations on the patient's skin where each respective allergen has been delivered, the device 10 may be provided with a marking unit 15, where the name of the allergen may be identified next to the respective allergen container 14. In this way, when the device 10 is applied to the skin of the patient, the response of the patient skin to each allergen may be easily identified, by means of the marking unit 15. For example, as shown in FIGS. 1 and 2, the container unit may be provided with eight allergen container 14 each containing a different allergen, the name of which is identified in the marking unit next to the respective allergen container 14. Each marking unit 15 may be releasably connected to the container unit 11 by means of a perforated line positioned on either side of the container unit 11. In this way, when the device is applied to the patient's skin 23, the marking unit 15 may be separated from the container unit 11 along the perforated lines, thereby remaining on the patient's skin after the container unit 11 has been removed. As a result, with the use of a marking unit 15, the skin response to the predetermined allergen may be easily identified. As shown in FIG. 2, the first surface 12 of the container unit 11 may be covered by a protective foil 16, which is arranged for sealing the container unit 11 so as to ensure the long term stability of the allergen contained in the allergen container 14. For example, the first surface 12 may be provided with a flexible adhesive layer 17 arranged for releasably securing the protective foil 16 on the first surface 12 of the container unit. Prior to attaching the device to the patient's skin 23, the protective foil 16 is removed, as shown in FIG. 2. Once the protective foil 16 is removed, the first surface 12 of the container unit 11 is exposed, as shown in FIG. 3. In this way, when the device 10 is attached to the patient's skin 23, by means of the flexible adhesive layer 17, the allergen containers 14 may be arranged for coming into contact with the skin of the patient. According to embodiments of the present invention, the protective foil 16 may be made from a non-absorbent material such as polyethylene, polypropylene, aluminium, and the like. In this way, it is ensured that the stability and concentration of the allergen are maintained within acceptable levels during storage of the device, since any absorption of the allergen by the protective foil 16 is prevented.

Figure 4:
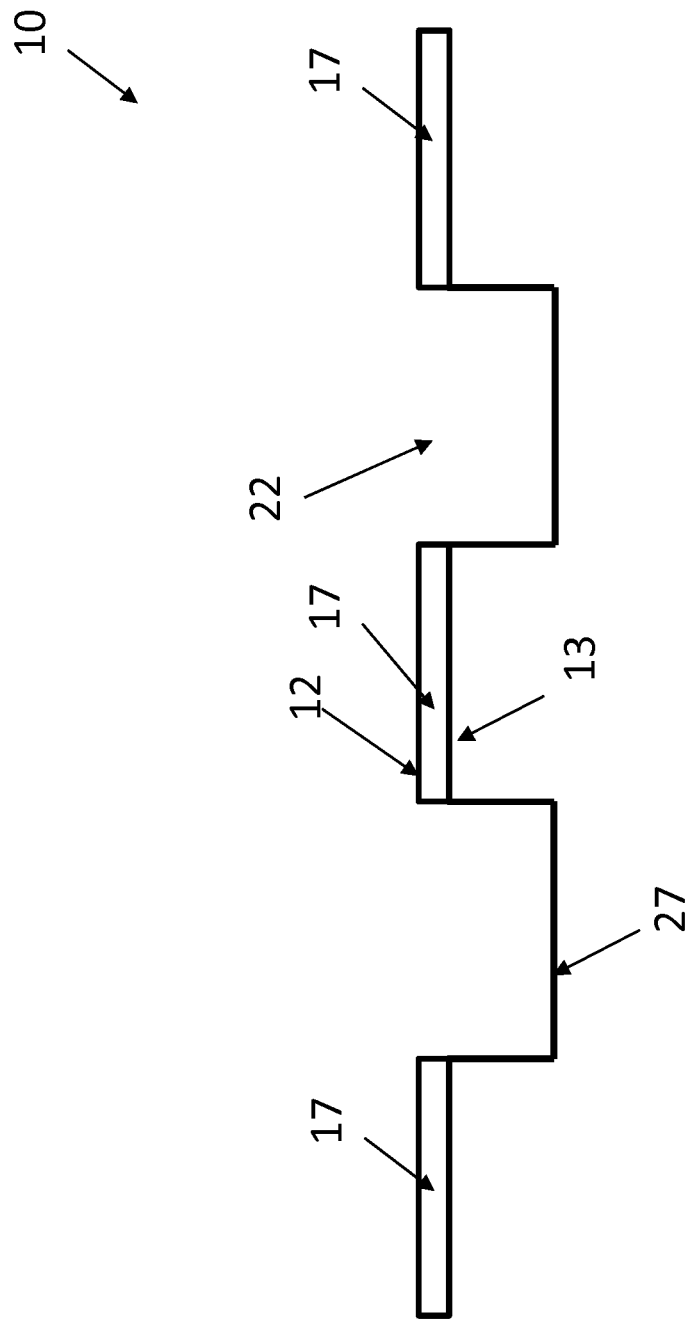
FIG. 4 shows schematically a cross-section of the device of FIG. 3 provided without the allergen container at points A-A'.

FIG. 4 shows schematically a cross-section of the device 10, shown in FIG. 3, along the point A-A', with the allergen containers 14 and protective foil 16 removed. As previously discussed, the container unit 11 may be provided with a plurality of cavity 22, each provided with a bottom wall 27, which may protrude from the second surface 13. The first surface 12 may be provided with a flexible adhesive layer 17, which may be made from any suitable material known to the skilled person in the art, arranged for releasably securing the device 10 on the patient's skin 23. For example, the flexible adhesive layer 17 may be made from similar materials to the ones mentioned in CN102908123 with regards to the respective flexible adhesive/paste layer. Each cavity 22 may be arranged for receiving an allergen container 14 containing a predetermined allergen in a predetermined concentration, e.g. in a predetermined registered concentration. Each allergen container 14 may be arranged for being releasably secured in the cavity 22 such that it can be easily removed and replaced from the container unit 11. For example, the flexible adhesive layer 17 may be arranged for releasably securing each allergen container 14 to the container unit. The container unit 11 may be made from a single material or a combination of materials such as Aluminium, polyethelene, polyamide and the like. According to embodiments of the present invention, the container unit may be designed as a generic container unit 11 that can be used with suitable allergen containers irrespective of the allergen concentration.

Figure 5:
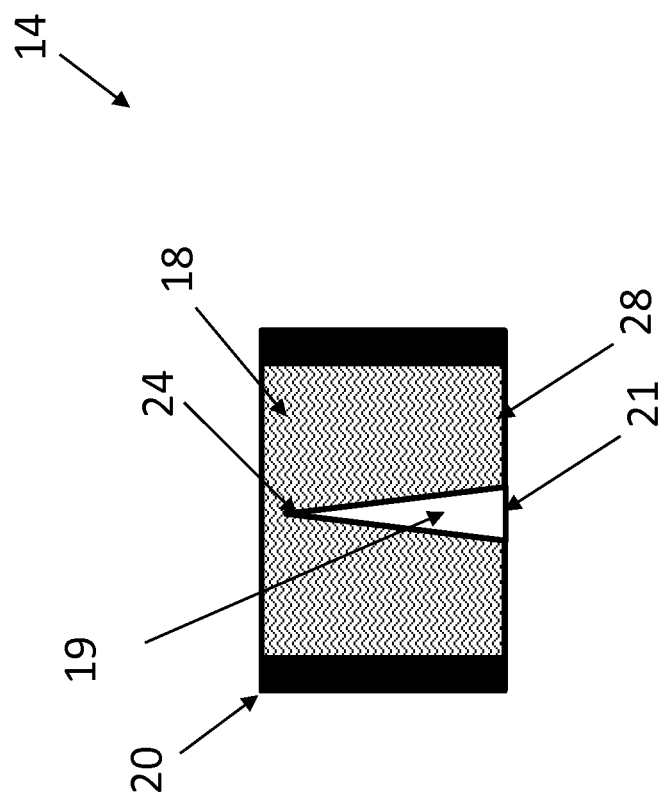
FIGS. 5 and 7 show schematically exemplified implementations of an allergen container according to embodiments of the present invention.
Figure 6:
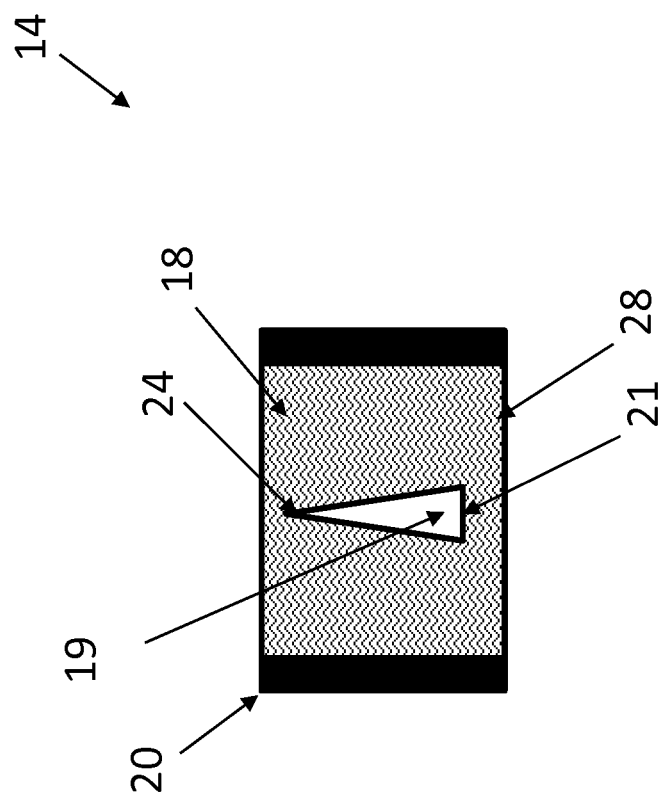
Figure 7:
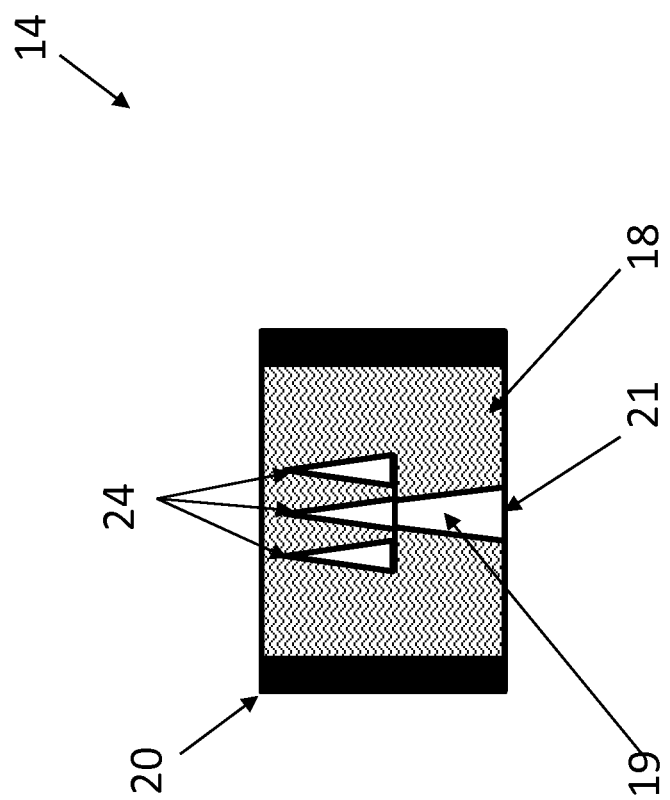

FIGS. 5 to 7 show exemplified implementations of the allergen container 14 according to embodiments of the present invention. The allergen container may be provided with a supporting material 18 and a pricking tool 19. The pricking tool 19 may be provided with a pricking tip 24 and a pricking base 21. For example and without any limitations, the pricking tool base may be secured at a location of the supporting material 18, e.g. at the bottom surface 28 of the supporting material 18. It should be understood that the pricking tool 19 may be secured at other locations of the supporting material 18, e.g. at a location within the supporting material 18, as shown in FIG. 6. The pricking tool 19 may be a needle or any other type of pricking tool 19 known to the skill person in the art that can penetrate or scratch the patient's skin surface 23 so that the allergen can be delivered to the patient's skin 23. In order to increase the skin response to the allergen, the pricking tool 19 e.g. the needle, may be provided with a plurality of pricking tips 24. For example and without any limitation, the pricking tool 19 may be provided with three pricking tips 24, as shown in FIG. 7. For example, by providing a pricking tool 19 with a plurality of tips 24, the patient's skin is penetrated at multiple closely spaced locations, thereby allowing the allergen to be delivered more effectively and in higher amounts to the skin, thereby optimising the skin response to the allergen. For example, by providing a pricking tool 19 with four tips 24, the amount of allergen delivered to the skin would be four times higher compared to the same allergen being delivered by a pricking tool 19 having only one tip 24. Moreover, a pricking tool 19 with a plurality of tips 24 may increase the skin response to allergens provided at low concentrations because it allows a higher quantity of the allergen to be delivered to the skin. Furthermore, the pricking tool 19, e.g. the needle, may be provided with a hollow body, thereby forming a canal opening. By providing the pricking tool 19 with a canal opening, the allergen may be more effectively delivered to the desired location on the patient's skin 23. The pricking tool 19 may be provided with a predetermined length. The pricking tool 19 may be positioned such that when the allergen container is positioned in the cavity 22, it's pricking tip or tips 24 face the opening of the cavity 22. According to embodiments of the present invention, the allergen container 14 may be provided with a frame 20, which may be arranged for surrounding the material 18, thereby forming the sidewall of the allergen container 14. For example, the frame 20 may be arranged for securing the supporting material 18 such that the pricking tool tip or tips 24 are maintained at the desired position during application of the device 10 to the patient's skin. Furthermore, the frame 20 may be arranged for limiting the wheel response of the patient's skin to the allergen. In this way, the wheel response is maintained within a confined area, thereby ensuring that the skin reaction is limited to a size which is easily identifiable, but not bothering the patient by strong itchy reactions, and additionally limiting the risk of large skin responses confluencing with other allergen areas. This may also limit the risk of systemic adverse events in the patient, as the allergen is hold at a confined area. According to embodiments of the present invention, the frame 20 may be made of a high density polyethylene material (HDPE). The frame 20 may be of any suitable shape arranged to conform to the shape of the cavity, such as circle, rectangular, square and the like.

According to embodiments of the present invention, the supporting material 18 may be made from a compressible material arranged when a force is applied for being compressed. For example, the supporting material 18 may be provided with a predetermined compressibility, such that in response a pressure change, e.g. a pressure force applied on a surface of the supporting material 18 by the thumb of a person, a relative change of the volume of the supporting material 18 is observed. The supporting material 18 may be made from any suitable material known to the skilled person in the art. For example, the supporting material 18 may be a spongy material, which may be made from any suitable material known to the skilled person in the art. For example, the spongy material may be made from a polymer based materials such as foam, sponge-like non-woven cotton fabric material such as fleece, and the like. Furthermore, the supporting material may be made from similar materials to the ones disclosed in CN102908123 with regards to spongy-like material. According to embodiments of the present invention, the supporting material 18 may be arranged for storing the allergen to be delivered to the patient's skin 23.

Figure 8:
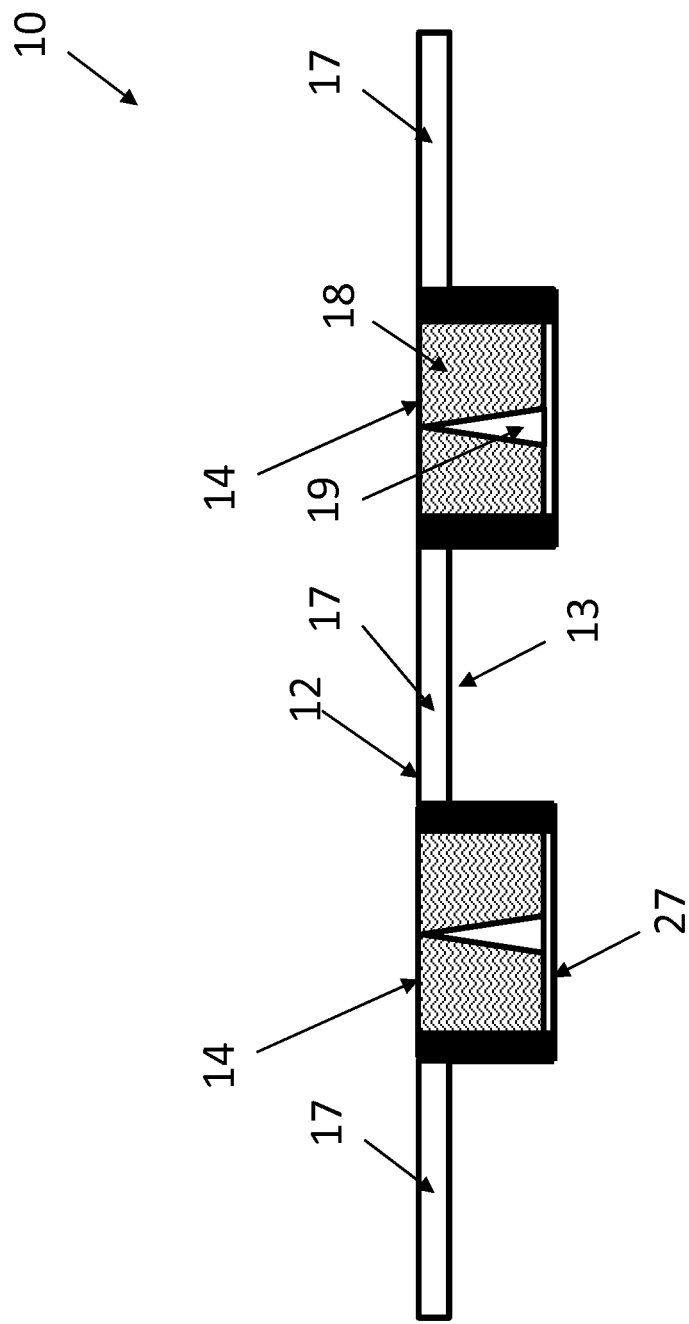
FIG. 8 shows schematically a cross-section of the device of FIG. 3 with the allergen containers releasably secured in respective cavities of the container unit at points A-A'.

FIG. 8 shows a cross-sectional view of an embodiment of the device 10 of FIG. 3 at the points A-A', with each allergen container 14 being positioned at a respective cavity 22. As previously discussed, the container unit 14 may be provided with a plurality of allergen containers 14, each positioned at a respective cavity 22. Each allergen container may be releasably secured in the cavity, so that they are maintained in the cavity 22 during the application of the device 10 to the patient skin 23 while being able to be removed if required. Furthermore, as previously discussed, each allergen container 14 may be provided with a predetermined allergen at a predetermined concentration. Each allergen container 14 may be optimised so that the allergen is delivered to the desired penetration depth, while ensuring that the first surface 12 of the device 10 is maintained substantially flat. Moreover, since the container unit 11 does not need to be adapted so that the penetration depth of each allergen container is optimised to the allergen concentration, the container unit 11 can be designed as a generic component, thereby reducing the cost and complexity of the manufacturing process of the device 10. Although it is shown in FIG. 8 that the supporting material is not in contact with the bottom wall 27 of the cavity, it should be understood that this is not a limitation and that the supporting material 18 in other embodiments of the present invention may be in contact with the bottom wall 27 of the cavity 22.

Figure 9:
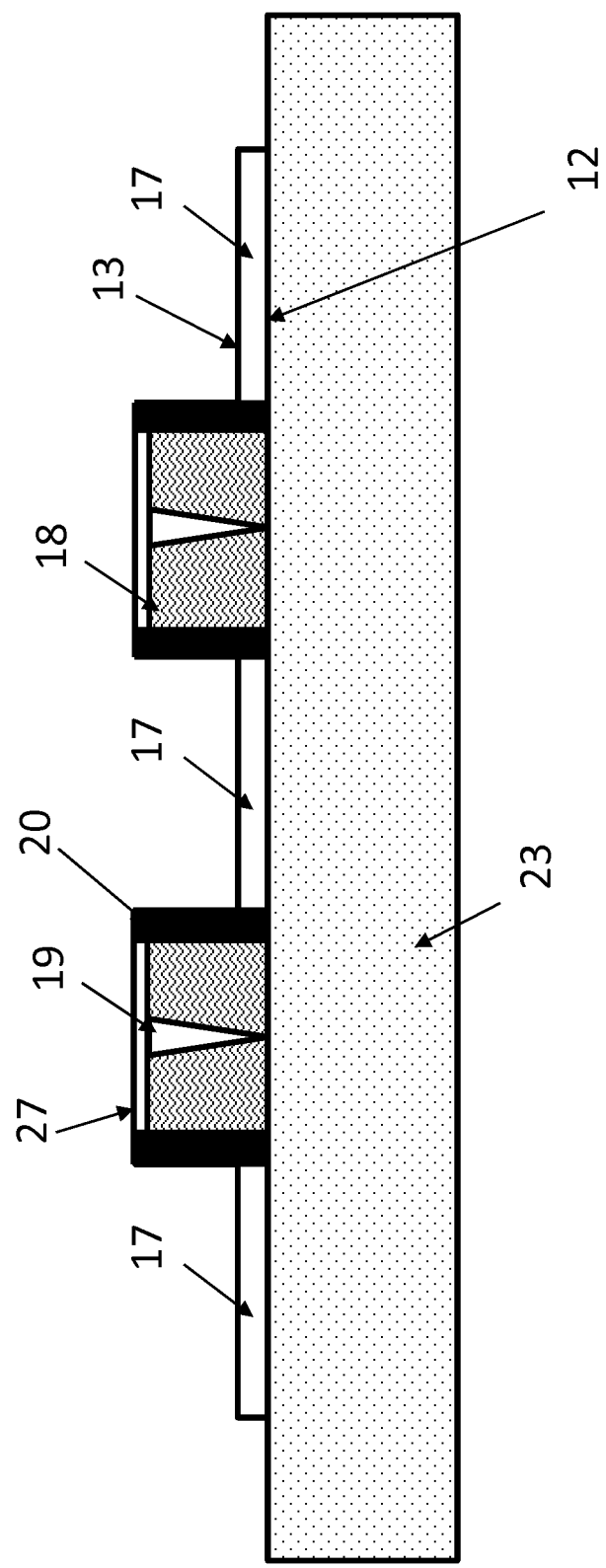
FIG. 9 shows schematically an example of a cross-section of the device of FIG. 3 when attached to the patient's skin.
Figure 10:
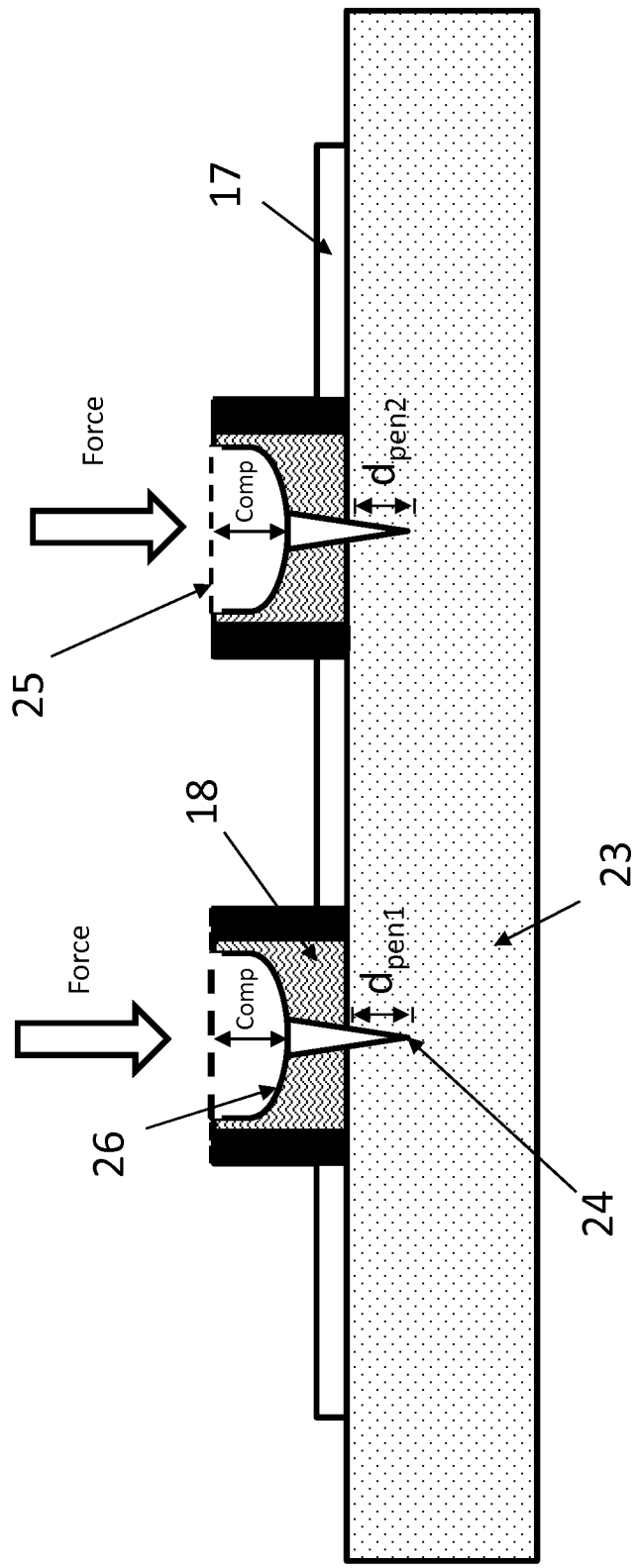
FIGS. 10 and 11 show schematically in respective cross-sectional views of the device the displacement of the pricking tool when a force is applied on the second surface.
Figure 11:
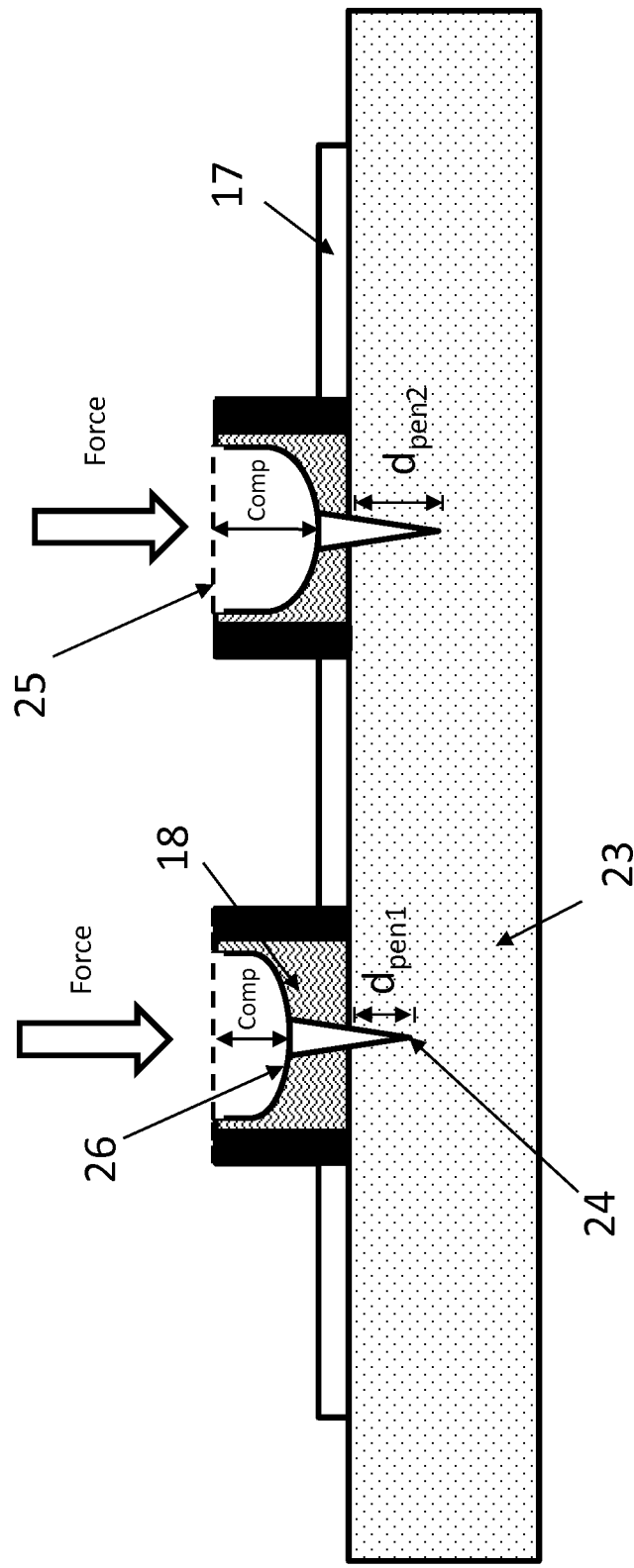

FIG. 9 shows an example of a cross-sectional view of the device 10 attached to the patient's skin 23. As shown, the first surface 12 is arranged for being in contact with the patient's skin 23. The allergen container 14 may be arranged such that their respective tips 24 are facing in the cavity 22 opening. As previously discussed, the supporting material 18 may be arranged, when a pressure force is applied on the second surface 13 of the device 10, for being compressed, as shown in FIG. 10. For example, when a pressure force is applied on the second surface 13 at the location of the bottom wall 27 of each respective cavity 22 in the container unit 11, it causes the bottom wall 27 of the cavity 22 to deform, thereby compressing the supporting material 18. Because the pricking tool 19 is secured at location of the supporting material 18, e.g. releasably secured at the bottom surface 28 of the supporting material 18, the pricking tool 19 is displaced from a first position 25, wherein at said first position 25 the at least one pricking tip 24 is at a first distance from the first surface 12, to a second position 26, wherein at said second position 26 the at least one pricking tip 24 is at a second distance from the first surface 12. As a result, due to the compression of the support material 18, the pricking tool 19 is displaced from the first position 25 to the second position 26 thereby penetrating the patient's skin 23 to a predetermined penetration depth, as shown in FIG. 10. The penetration depth may be defined by the distance by which the pricking tip 24 extends over the first surface 12 when the pricking tool is at the second position 26. In order to optimise the penetration depth to the allergen concentration, each allergen container 14 may be adapted such that at the second position 26 the pricking tip 24 extends over the first surface 12 by a predetermined distance. For example, in the case where each allergen container is provided with an allergen at the same concentration, the allergen containers 14 may be adapted such that the penetration depth, dpen, achieved at the location of each respective allergen container is substantially equal, as shown in FIG. 10. Furthermore, with the present invention it is possible to provide the container unit 11 with allergen containers 14 that have been optimised to deliver their respective allergens at different penetration depths while ensuring that the first surface remains substantially flat, as shown in FIG. 11. In the case where the allergen is stored in the supporting material 18, during compression of the material, the allergen flows along the length of the pricking tool 19 so that it is delivered to the pricking tip or tips 24, thereby allowing for the allergen to be delivered at the desired location in the patient skin 23.

Furthermore, in the case where the pricking tool is provided with a canal opening, the allergen may be arranged to flow through the canal opening to the pricking tip so that the allergen is delivered to the patient's skin.

According to embodiments of the present invention, by controlling the range of the displacement of the pricking tool 19 from the first position 25 to the second position 26, the penetration depth may be optimised to the concentration of the allergen to be delivered. The range of displacement may be optimised by adapting the parameters of the allergen container 14, such as the height and/or compressibility of the supporting material 18, and/or the length of the pricking tool 19. For example, since the pricking tool 19 is arranged for being secured at a location of the supporting material 18, its range of displacement may be controlled by the characteristics of the supporting material. In this way, based on the penetration depth required, the allergen container 14 may be provided with a supporting material 18 having a predetermined compressibility that has being chosen, when compressed to displace the pricking tool 19 to the desired penetration depth. For example in the case where a higher penetration depth is required, the supporting material may be changed to a supporting material having higher compressibility in response to the same pressure force, e.g. the pressure force that can be affected by the thumb of a person. Furthermore, the height of the supporting material 18 may be chosen such that at the second position 26 the pricking tip 24 of the pricking tool 19 extends over the first surface 12 by a predetermined distance. For example, in the case where a smaller penetration depth is required, the allergen container 14 may be provided with a supporting material 18 having a shorter length. Moreover, the length of the pricking tool may be chosen such that at the second position 26 the pricking tip 24 extends over the first surface 12 by a predetermine distance. For example, the length of the pricking tool 19 may be chosen based on the compressibility and height of the supporting material 18 and concentration of the allergen.

According to embodiments of the present invention, at the second position 26 the pricking tip 24 may be arranged for extending over the first surface 12 by a distance of preferably between 0.5 mm and 1.2 mm, more preferably between 0.7 mm to 1.0 mm, and even more preferably 0.8 mm. For example and without any limitation, in order to optimise the allergen container 14 so that at the second position 26 the pricking tip 24 extends over the first surface by 0.8 mm, the supporting material 18 may be arranged for being compressed by 0.8 mm.

According to embodiments of the present invention, in order to ensure the stability and concentration of the allergen, the support material 18 and/or the protective foil 16 may be provided with a coating layer. For example, the coating layer may comprise allergen or human serum albumin up to 2%. The coating layer may comprise any of streptavidin-biotin, streptavidin-horseradish peroxidase, sugars, two component polymer mix or silicone. The allergen may comprise glycerol up to 50% or Triton-X 100 to keep the allergen in solution and avoid adsorption to the supporting material 18 or foil 16.

According to embodiments of the present invention, and without any limitation the device 10 may be implemented as follows:

- Container unit 11 with cavities 22 having a thickness around 90-100 μm and made of Polyamide (20 μm)+Aluminium (50 μm)+Polyelthylene(20 μm).
- Flexible adhesive layer 17 made of Polyethylene (PE) foam having a thickness of around 1.24 mm double-sided bandage thickness 0.11 mm
- Frame 20 made of high density polyethylene (HDPE) having a height of around 2 mm, an inner diameter of 10 mm, and an outer diameter of 13 mm.
- Supporting material 18 made from a fleece non-woven polymer having height of 2 mm, and when compressed a height of 1.2 mm
- Needle 19 made of stainless steel and having a height of 2 mm.
- Protective foil 16 made of Aluminium and having a thickness of 90-100 μm
- allergen solutions contained in the allergen container 14 having an allergen concentration of 10 HEP (10.000 BU/ml).

LIST OF REFERENCE NUMBERS

10 Device for performing an allergy test
11 Container unit
12 First surface
13 Second surface
14 Allergen container
15 Marking unit
16 Protective foil
17 Flexible adhesive layer
18 Supporting material
19 Pricking tool
20 Frame
21 Pricking tool base
22 Cavity
23 Patient's skin
24 Pricking tip
25 first position of the pricking tool
26 Second position of the pricking tool
27 Bottom wall of cavity
28 Bottom surface of supporting material

The invention claimed is:

1. A device for performing an allergy test for type I immune reactions, the device comprising:

a container unit having a substantially flat first surface configured to contact the skin of a patient undergoing the allergy test and a second surface opposite to the first surface, the container unit comprising a plurality of cavities each configured to receive an allergen container having an allergen in a concentration, the allergen container comprising a supporting material and a pricking tool having a pricking tip facing in the direction of a cavity opening, the pricking tool having a length;

wherein the pricking tool is positioned adjacent the supporting material, the supporting material configured to be compressed when a pressure force is applied on the second surface of the container unit, thereby causing the pricking tool to be displaced from a first position, wherein the pricking tip is at a first distance from the first surface, to a second position, wherein the pricking tip is at a second distance from the first surface, wherein the allergen container is provided with a frame forming the sidewall of the allergen container surrounding the supporting material, and wherein the allergen container is separate from the container unit comprising the plurality of cavities.

2. The device according to claim 1, wherein the supporting material is configured to control the range of displacement of the pricking tool between the first and second positions.

3. The device according to claim 1, wherein each allergen container is adapted such that at the second position the pricking tip of the pricking tool extends beyond the first surface of the container unit by a distance defining a penetration depth of the pricking tool in the patient's skin.

4. The device according to claim 1, wherein compressibility of the supporting material in each allergen container is selected such that at the second position the pricking tip of the pricking tool extends beyond the first surface by a distance.

5. The device according to claim 1, wherein a height of the supporting material in each allergen container is selected such that at the second position the pricking tip of the pricking tool extends beyond the first surface by a distance.

6. The device according to claim 1, wherein the length of the pricking tool in each allergen container is selected based on compressibility and height of the supporting material and concentration of the allergen, such that at the second position, the pricking tip of the pricking tool extends beyond the first surface by a distance.

7. The device according to claim 1, wherein at the second position, the pricking tip is configured to extend beyond the first surface by a distance of between about 0.5 mm and about 1.2 mm.

8. The device according to claim 1, wherein the support material is selected from a group consisting of a spongy material and a fleece material.

9. The device according to claim 1, wherein the pricking tool comprises a needle having the pricking tip.

10. The device according to claim 9, wherein the needle comprises a hollow body forming a canal opening.

11. The device according to claim 9, wherein the needle comprises a plurality of pricking tips.

12. The device according to claim 9, wherein the needle comprises at most three pricking tips.

13. The device according to claim 1, wherein the first surface of the container unit comprises a flexible adhesive layer configured to releasably secure the device on the patient's skin.

14. The device according to claim 13, wherein the device further comprises a protective foil releasably secured on the first surface of the container unit by the flexible adhesive layer.

15. The device according to claim 13, wherein the flexible adhesive layer is additionally configured to releasably secure the allergen container to the container unit.

16. The device according to claim 14, wherein the protective foil comprises a non-absorbent material.

17. The device according to claim 16, wherein the non-absorbent material is selected from the group consisting of polyethylene, polypropylene, and aluminium.

18. The device according to claim 14, further comprising a coating layer associated with one or more of the support material or the protective foil.

19. The device according to claim 18, wherein the coating layer comprises one of allergen or human serum albumin up to 2%.

20. The device according to claim 18, wherein the coating layer comprises one or more of streptavidin-biotin, streptavidin-horseradish peroxidase, sugars, two component polymer mix, or silicone.

21. The device according to claim 1, wherein the allergen comprises one of glycerol up to 50% or Triton-X 100.

22. The device according to claim 1, wherein at the second position, the pricking tip is configured to extend beyond the first surface by a distance of between about 0.7 mm and about 1.0 mm.

23. The device according to claim 1, wherein at the second position, the pricking tip is configured to extend beyond the first surface by a distance of about 0.8 mm.

* * * * *